US00PP19420P2

(12) United States Plant Patent
van der Meer

(10) Patent No.: US PP19,420 P2
(45) Date of Patent: Nov. 4, 2008

(54) ***CHRYSANTHEMUM* PLANT NAMED 'KISTAR DARK'**

(50) Latin Name: *Chrysanthemum×morifolium*
Varietal Denomination: Kistar Dark

(75) Inventor: Adrianus L. M. van der Meer, Monster (NL)

(73) Assignee: Beekenkamp Plants B.V., Maasdijk (NL)

( * ) Notice: Subject to any disclaimer, the term of this patent is extended or adjusted under 35 U.S.C. 154(b) by 0 days.

(21) Appl. No.: 11/787,686

(22) Filed: Apr. 16, 2007

(51) Int. Cl.
*A01H 5/00* (2006.01)

(52) U.S. Cl. ..... Plt./290

(58) Field of Classification Search ..... Plt./290
See application file for complete search history.

*Primary Examiner*—Kent L. Bell
*Assistant Examiner*—Georgia Helmer
(74) *Attorney, Agent, or Firm*—C. A. Whealy

(57) ABSTRACT

A new and distinct cultivar of *Chrysanthemum* plant named 'Kistar Dark', characterized by its compact, upright and mounded plant habit; dark green-colored foliage; uniform flowering response; early flowering habit; freely flowering habit; decorative-type inflorescences with dark orange-colored ray florets; and good postproduction longevity.

1 Drawing Sheet

Botanical designation: *Chrysanthemum×morifolium.*
Cultivar denomination: 'Kistar Dark'.

BACKGROUND OF THE INVENTION

The present invention relates to a new and distinct cultivar of *Chrysanthemum* plant, botanically known as *Chrysanthemum×morifolium,* commercially grown as a potted *Chrysanthemum* and hereinafter referred to by the name 'Kistar Dark'.

The new *Chrysanthemum* is a naturally-occurring branch mutation of the *Chrysanthemum×morifolium* cultivar Kistar, not patented. The new *Chrysanthemum* was discovered by the Inventor on a single flowering plant in a population of plants of 'Kistar' in a controlled environment in Monster, The Netherlands in September, 2005.

Asexual reproduction of the new *Chrysanthemum* by vegetative tip cuttings was first conducted in 's-Gravenzande, The Netherlands in November, 2005. Asexual reproduction by cuttings has shown that the unique features of this new *Chrysanthemum* are stable and reproduced true to type in successive generations.

SUMMARY OF THE INVENTION

Plants of the cultivar Kistar Dark have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Kistar Dark'. These characteristics in combination distinguish 'Kistar Dark' as a new and distinct potted *Chrysanthemum* cultivar:

1. Compact, upright and mounded plant habit.
2. Dark green-colored foliage.
3. Uniform flowering response.
4. Early flowering habit, eight-week response time.
5. Freely flowering habit.

6. Decorative-type inflorescences with dark orange-colored ray florets.
7. Good postproduction longevity with plants maintaining good substance and color for about four to five weeks in an interior environment.

Plants of the new *Chrysanthemum* differ from plants of the parent, the cultivar Kistar, primarily in leaf and ray floret coloration as plants of the new *Chrysanthemum* have darker colored leaves and ray florets than plants of the cultivar Kistar.

Plants of the new *Chrysanthemum* can be compared to plants of the *Chrysanthemum* cultivar Kilargo, not patented. In side-by-side comparisons conducted in Monster, The Netherlands, plants of the new *Chrysanthemum* differed from plants of the cultivar Kilargo in the following characteristics:

1. Plants of the new *Chrysanthemum* and the cultivar Kilargo differed slightly in leaf coloration.
2. Inflorescences of plants of the new *Chrysanthemum* and the cultivar Kilargo differed in ray floret coloration as plants of the cultivar Kilargo had red purple-colored ray florets.

BRIEF DESCRIPTION OF THE PHOTOGRAPHS

The accompanying photographs illustrate the overall appearance of the new *Chrysanthemum.* These photographs show the colors as true as it is reasonably possible to obtain in colored reproductions of this type. Colors in the photographs may differ slightly from the color values cited in the detailed botanical description which accurately describe the colors of the new *Chrysanthemum.*

The photograph at the top of the sheet comprises a side perspective view of typical flowering plant of 'Kistar Dark'.

The photograph at the bottom of the sheet is a close-up view of the upper (left) and lower (right) surfaces of typical leaves and inflorescences of 'Kistar Dark'.

DETAILED BOTANICAL DESCRIPTION

The aforementioned photographs and following observations and measurements describe plants grown during the spring in 's-Gravenzande, The Netherlands during the winter in a glass-covered greenhouse and under conditions and practices which approximate those generally used in commercial potted *Chrysanthemum* production. During the production of the plants, day and night temperatures were about 17° C. to 18° C. Plants were grown under photoinductive short day/long night treatments. Plants used in the photographs and for the description were not pinched and were about ten weeks old. In the following description, color references are made to The Royal Horticultural Society Colour Chart, 2001 Edition, except where general terms of ordinary dictionary significance are used.

Botanical classification: *Chrysanthemum×morifolium* cultivar Kistar Dark.

Parentage: Naturally-occurring branch mutation of the *Chrysanthemum×morifolium* cultivar Kistar, not patented.

Propagation:

*Type.*—Terminal vegetative cuttings.

*Time to initiate roots, summer.*—About six days at temperatures of about 20° C.

*Time to initiate roots, winter.*—About seven days at temperatures of about 20° C.

*Time to produce a rooted young plant, summer.*—About 14 days at temperatures of about 20° C.

*Time to produce a rooted young plant, winter.*—About 16 days at temperatures of about 20° C.

*Root description.*—Fine; light brown in color.

*Rooting habit.*—Freely branching; moderately dense.

Plant description:

*Appearance.*—Herbaceous compact decorative-type potted *Chrysanthemum.* Stems upright and slightly outwardly spreading giving a mounded appearance to the plant. Moderately vigorous growth habit. Freely branching, about four lateral branches develop per plant.

*Plant height.*—About 11 cm to 13 cm.

*Plant width.*—About 12 cm.

*Lateral branches.*—Length: About 4 cm to 6 cm. Diameter: About 2 mm to 3 mm. Internode length: About 1 mm to 5 mm. Strength: Moderately strong to strong. Texture: Pubescent. Color: Close to 144B.

Foliage description:

*Arrangement.*—Alternate, simple.

*Length.*—About 5.5 cm to 6.5 cm.

*Width.*—About 3.5 cm to 4 cm.

*Apex.*—Mucronulate.

*Base.*—Attenuate.

*Margin.*—Palmately lobed, sinuses between lateral lobes parallel to divergent.

*Texture, upper and lower surfaces.*—Pubescent; slightly rough; veins prominent on lower surface.

*Color.*—Developing foliage, upper surface: Close to 137A. Developing foliage, lower surface: Close to 137C to 137D. Fully expanded foliage, upper surface: Close to 147A; venation, close to 146B. Fully expanded foliage, lower surface: Close to 147B; venation, close to 146B.

*Petiole length.*—About 7 mm to 1.2 cm.

*Petiole diameter.*—About 1.5 mm to 2 mm.

*Petiole texture, upper and lower surfaces.*—Slightly pubescent.

*Petiole color, upper and lower surfaces.*—Close to 146B.

Inflorescence description:

*Appearance.*—Decorative-type inflorescence form with oblong-shaped ray florets. Inflorescences borne on terminals above foliage. Disk and ray florets arranged acropetally on a capitulum. Inflorescences slightly fragrant.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering habit; plants flower about eight weeks later.

*Postproduction longevity.*—Inflorescences maintain good color and substance for about four to five weeks in an interior environment.

*Quantity of inflorescences.*—Freely flowering, about twelve inflorescences develop per plant.

*Inflorescence bud.*—Height: About 2.5 mm. Diameter: About 4 mm. Shape: Oblate. Color: Between 144A and 144D.

*Inflorescences.*—Diameter: About 2.5 cm to 3 cm. Depth (height): About 1.5 cm. Diameter of disc: About 2 mm. Receptacle diameter: About 2 mm. Receptacle height: About 1.5 mm.

*Ray florets.*—Shape: Oblong. Orientation: Initially upright, then about 90° from vertical or perpendicular to peduncle. Aspect: Initially incurved, then mostly flat. Length: About 1.2 cm. Width: About 5 mm. Apex: Rounded to emarginate. Base: Attenuate. Margin: Entire. Texture, upper and lower surfaces: Smooth, glabrous, satiny. Number of ray florets per inflorescence: About 70 arranged in six to eight whorls. Color: When opening, upper surface: Close to 172A, but more reddish in color. When opening, lower surface: Close to 164B. Fully opened, upper surface: Close to N172A. Fully opened, lower surface: Close to 163C.

*Disc florets.*—Arrangement: Massed at center of receptacle. Shape: Tubular, elongated. Apex: Five-pointed. Length: About 4 mm to 5 mm. Width: About 1 mm. Number of disc florets per inflorescence: About one to three. Color, immature and mature: Apex: Close to 14B. Mid-section: Close to 145C to 145D. Base: Close to 145D.

*Phyllaries.*—Number of phyllaries per inflorescence: About 20. Length: About 6 mm. Width: About 3 mm to 4 mm. Shape: Oval. Apex: Rounded. Base: Rounded to truncate. Texture, upper and lower surfaces: Smooth, glabrous. Color, upper and lower surfaces: Close to 137C.

*Peduncles.*—Length: First peduncle: About 1 cm to 1.5 cm. Fourth peduncle: About 2 cm to 2.5 cm. Diameter (first peduncle): About 1 mm. Angle: About 30° from vertical. Strength: Moderately strong, flexible. Texture: Pubescent. Color: Close to 137C.

*Reproductive organs.*—Androecium: None observed. Gynoecium: Present on both ray and disc florets. Stigma shape: Bi-parted. Stigma color: Close to 14B. Style length: About 4 mm. Style color: Close to 4D.

*Seed/fruit.*—Seed and fruit production has not been observed.

Disease/pest resistance: Resistance to pathogens and pests common to *Chrysanthemums* has not been observed on plants grown under commercial conditions.

Temperature tolerance: Plants of the new *Chrysanthemum* have demonstrated good tolerance to low temperatures of about 5° C. and high temperatures of about 30° C.

It is claimed:

1. A new and distinct *Chrysanthemum* plant named 'Kistar Dark' as illustrated and described.

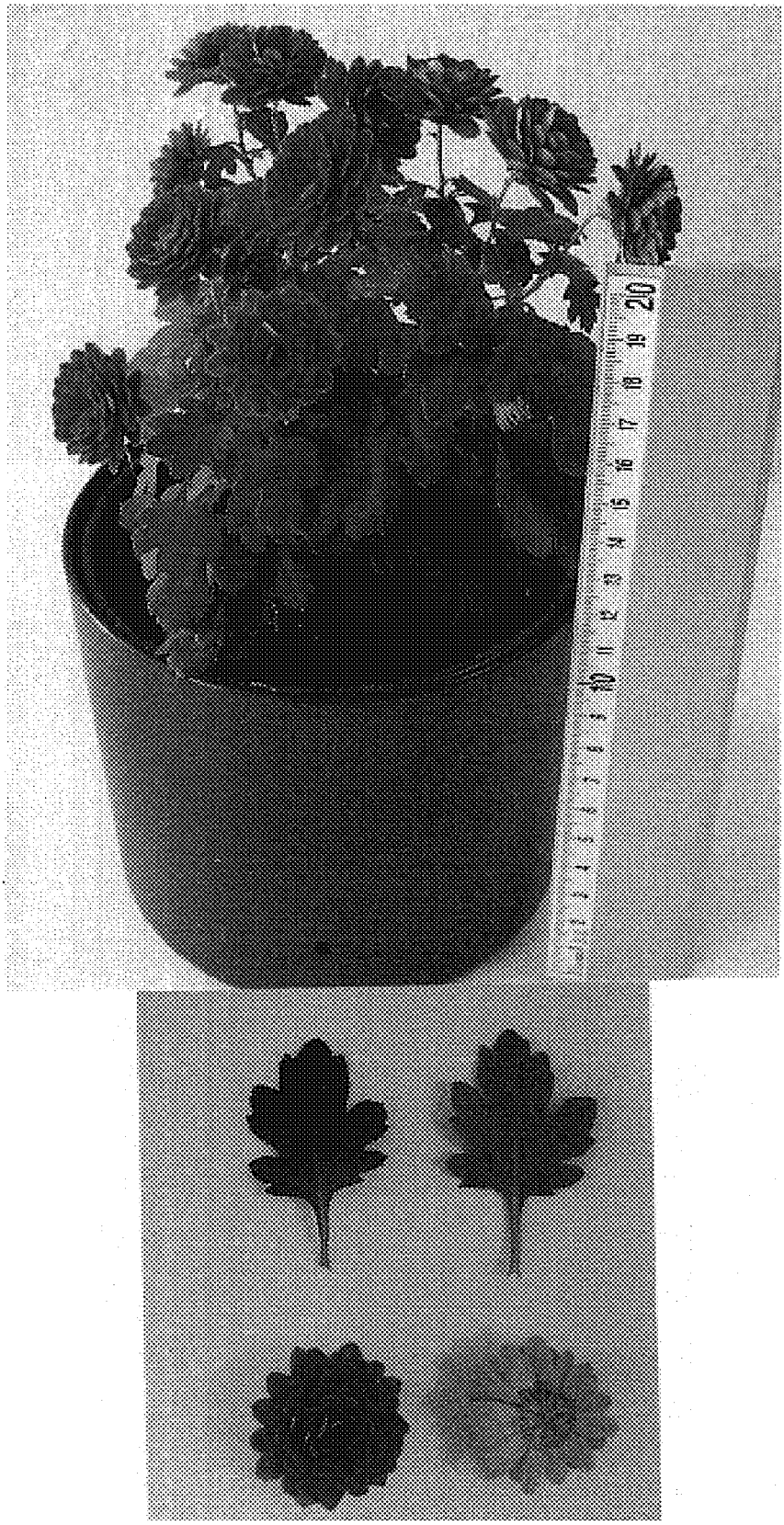

* * * * *